United States Patent [19]

Hon

[11] Patent Number: 4,947,853
[45] Date of Patent: Aug. 14, 1990

[54] SENSOR SUPPORT BASE AND METHOD OF APPLICATION

[76] Inventor: Edward H. Hon, 11 Bradbury Hills Rd., Bradbury, Calif. 91010

[21] Appl. No.: 118,441

[22] Filed: Nov. 9, 1987

Related U.S. Application Data

[63] Continuation-in-part of Ser. No. 915,130, Oct. 12, 1986, which is a continuation-in-part of Ser. No. 780,398, Sep. 26, 1985, and a continuation-in-part of Ser. No. 858,713, May 2, 1986, abandoned.

[51] Int. Cl.⁵ .................................................. A61B 8/00
[52] U.S. Cl. .............................. 128/662.03; 128/775; 128/802
[58] Field of Search ............................. 128/774–775, 128/778, 780, 782, 721, 660.02, 661.07, 662.03–662.04, 639–640

[56] References Cited

U.S. PATENT DOCUMENTS

| | | | |
|---|---|---|---|
| 3,520,294 | 7/1970 | Fuzzell et al. | 128/775 |
| 3,568,663 | 3/1971 | Phipps | 128/643 |
| 3,824,988 | 7/1974 | Soldner et al. | 128/662.04 |
| 3,913,563 | 10/1975 | Ball | 128/775 |
| 3,945,373 | 3/1976 | Tweed et al. | 128/778 X |
| 4,122,837 | 10/1978 | Leonard | 128/774 |
| 4,355,643 | 10/1982 | Laughlin et al. | 128/662.04 |
| 4,483,344 | 11/1984 | Atkov et al. | 128/662.03 |
| 4,556,066 | 12/1985 | Semrow | 128/662.03 |
| 4,640,295 | 2/1987 | Isaacson | 128/775 X |

OTHER PUBLICATIONS

Clare; WO 0003115; 6-1986.

Primary Examiner—Angela D. Sykes
Attorney, Agent, or Firm—Lewis Anten

[57] ABSTRACT

An improved sensor support base having a relatively flexible portion around its periphery, a highly absorbent material on the lower surface and a means for deforming the support base is disclosed. The support base is adhesively applied to the abdomen and is used in monitoring labor contractions of a patient.

46 Claims, 4 Drawing Sheets

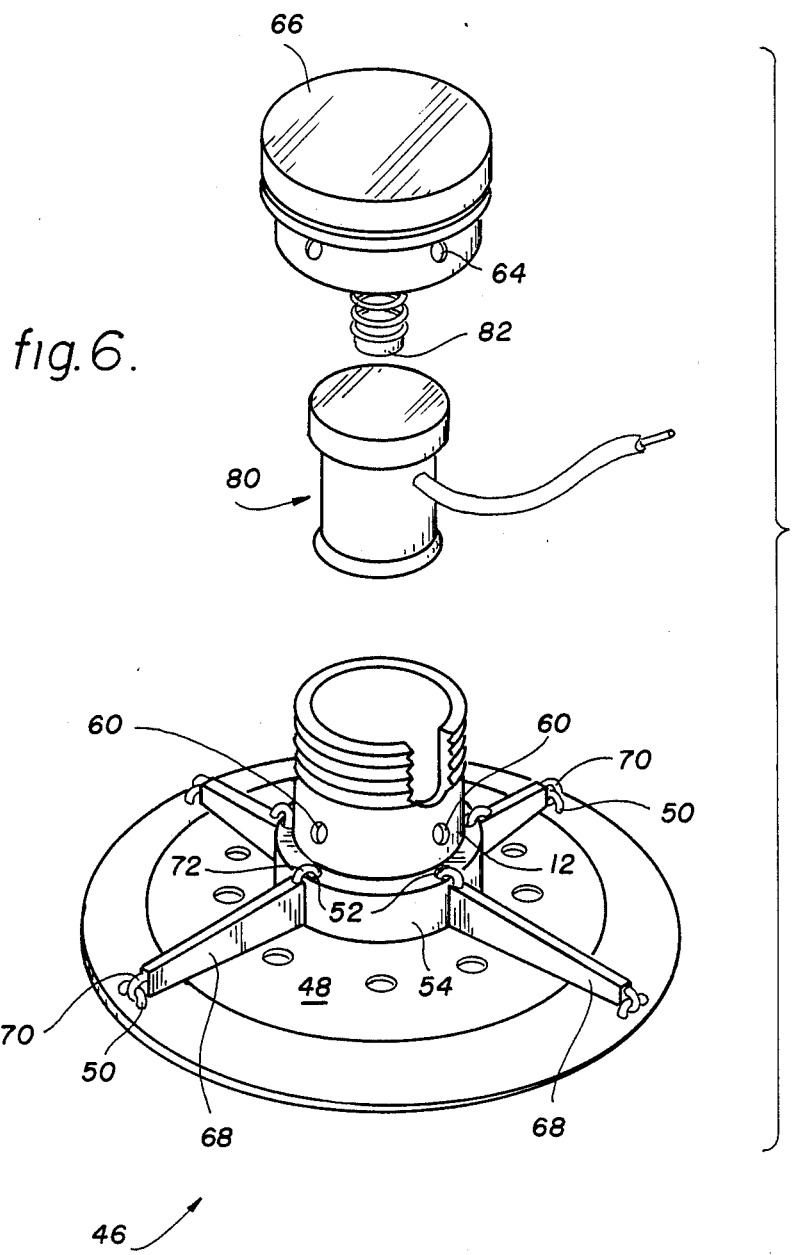

4,947,853

SENSOR SUPPORT BASE AND METHOD OF APPLICATION

RELATED APPLICATIONS

This is a continuation-in-part of patent application entitled External Uterine Contraction Monitoring Device, Ser. No. 915,130, filed by Edward H. Hon, Edward D. Hon and Robert W. Hon, on Oct. 2, 1986, pending which was a continuation-in-part of patent application CONTINUOUS CUTANEOUS BLOOD PRESSURE MEASURING APPARATUS AND METHOD, Ser. No. 780,398, pending filed by Edward H. Hon, M. D. and Edward D. Hon, on Sept. 26, 1985, and a continuation-in-part of patent application entitled Apparatus for Measuring Blood Pressure, Ser. No. 06/858,713, filed by Edward H. Hon, M.D. and Edward D. Hon, on May 2, 1986, now abandoned.

BACKGROUND OF THE INVENTION

In the co-pending application entitled External Uterine Contraction Monitoring Device, a support base for a monitoring device for monitoring the contractions of a patient in labor was disclosed. The apparatus consisted of a concave support base which was attached externally, by adhesive means, to the abdomen of the patient. The support base, once relatively fixedly attached, was then used to support a transducer means in place against the abdomen of the patient.

The previously disclosed support base was a single integral piece, with the support base being slightly thicker proximate the center of the support base, and gradually tapering to a thinner portion away from the center.

It has been found that the previously disclosed support base would, on occasion, lift up at the edges during use. This is undesirable since it could result, if the lifting was extensive, in loss of the original positioning of the transducer sensor in relationship to the abdomen.

Further, it became desirable to have a support base that would have a wider application of use so as to be able to be used on all sizes of patients.

It was also found that the previously disclosed support base was often difficult to remove from the patient after use.

OBJECTS OF THE PRESENT INVENTION

It is an object of the present invention to provide an improved support base for use in retaining a transducer against a patient, which is capable of withstanding greater lifting forces.

It is another object of the present invention to provide an improved support base, which is capable of being used on a wide variety of patients.

It is another object of the present invention to provide a support base that is easy to manufacture.

It is another object of the present invention to provide a support base which is easy to remove from the patient after use.

It is another object of the present invention to provide a support base that is more comfortable to the patient.

These and other objects of the present invention will be evident from the specification and the accompanying drawings.

SUMMARY OF THE INVENTION

The improved support base is substantially concave and consists of a first inner portion that is substantially rigid in relationship to a second outer portion which extends substantially around the periphery of the first portion. In the preferred embodiment the support base is circular.

The first relatively rigid inner portion is made of hard plastic, while the second relatively flexible outer portion is made of a soft plastic or rubber material. This permits the support base to fit a wide range of abdominal sizes from the relatively small to the very large. Also, the flexible outer portion, due to its flexibility, may be more easily lifted so as to permit the application of a solution for dissolving the adhesive application which adheres the support base to the patient.

The shape of the support base is capable of being changed, depending on the size of the patient, by means of support struts that maintain the support base in the desired deformed configuration.

Further details of the invention will be evident from a review of the following descriptions of the drawings and the detailed description of the invention.

BRIEF DESCRIPTION OF THE DRAWINGS

FIG. 6 is an exploded perspective view of an alternative embodiment of the support base.

DETAILED DESCRIPTION OF THE INVENTION

Figure 1:
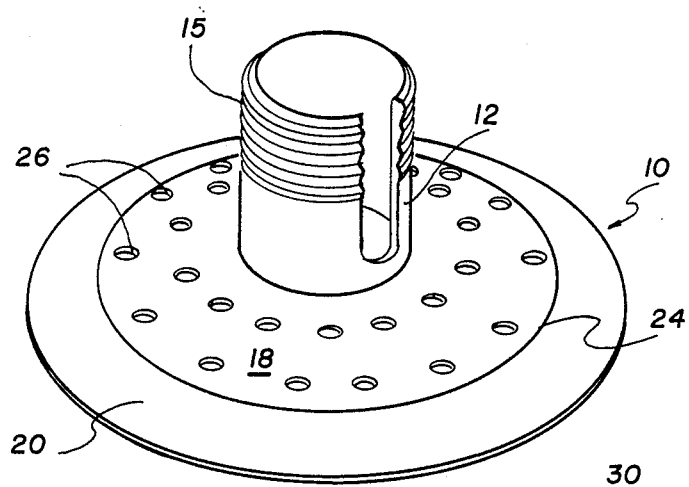
FIG. 1 is a top perspective view of the support base.
Figure 2:
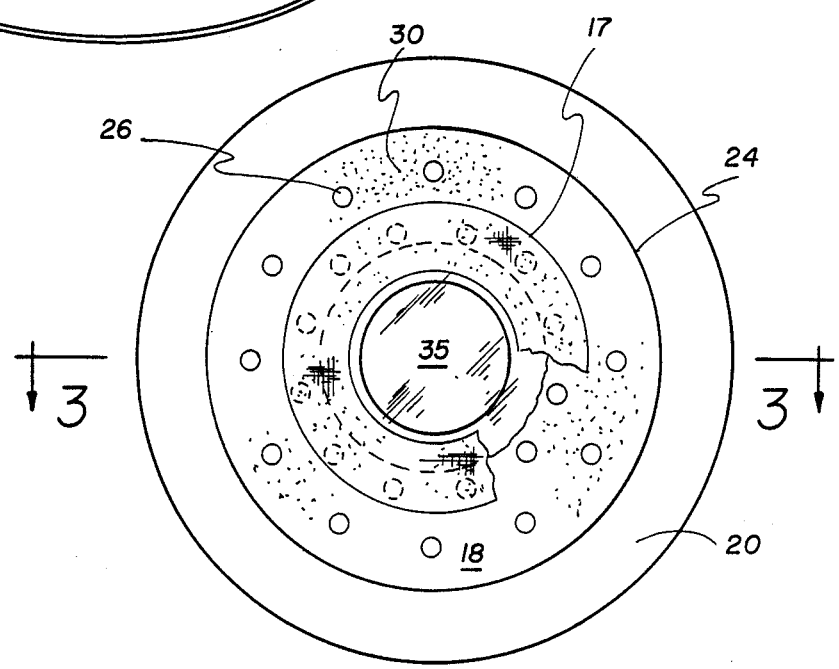
FIG. 2 is a bottom view of the support base.
Figure 3:
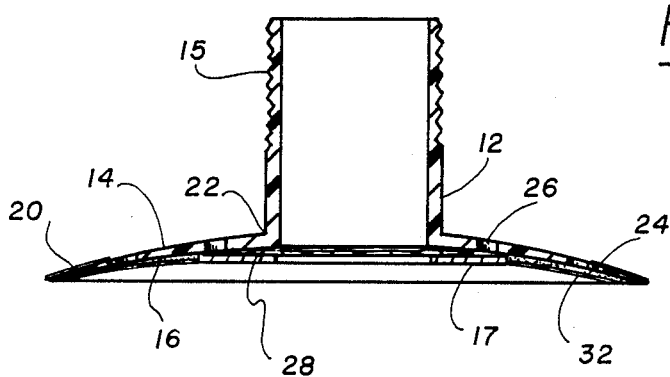
FIG. 3 is a side sectioned view of the support base taken along section lines 3—3 of FIG. 2.

Making reference to FIGS. 1-3, a substantially concave support base 10 is shown having an upstanding hollow tubular member 12 mounted perpendicular thereto, substantially at the center of the support base 10. The hollow tubular member 12 may be formed integrally with the support base or attached by other means, such as by threads, force fitting or other coupling means.

The tubular member 12 has an internal diameter of approximately 1 inch and has an external thread 15 for receiving a cap 66, shown in FIGS. 6 and 7. Slot 13 in tubular member 12 is adapted to permit electrical connections to pass through the wall of the member 12. The upper portion of the hollow tubular member extends approximately 1½ inches above the top surface 14 of the support base 10.

The support base 10 has a first inner portion 18 which is made of a relatively rigid plastic material and a second outer relatively flexible portion 20 made of a soft flexible rubber or plastic material. The support base 10 has a diameter large enough to provide a sufficient surface area in contact with the skin of the patient to withstand vertical lifting of the sensor support plate. It has been found that a diameter of 3 to 5 inches is highly acceptable, with the preferred diameter being about 5 inches. The use of the flexible outer portion requires that the support base be slightly larger than a support base without the flexible portion.

The second outer flexible portion 20 extends approximately ½ to 1 inch beyond the periphery of the first inner portion 18. The first inner portion 18 has a thickness of about ⅛ inch at its central portion proximate the joinder 22 of the hollow tubular member 12 and tapers to a thickness of about 1/10 inch at the location 24 that it joins the second outer portion 20.

The second outer portion 20 overlaps the first inner portion 18 to some extent, if molded in two steps, and is approximately the same thickness as the first inner portion 18 at the location of joinder 24. The second outer portion 20 tapers slightly at its outer periphery.

An adhesive layer 30 is attached to the bottom surface 16 of the support base which in turn is covered by a removable paper backing sheet 32.

A series of openings 26 are formed in the support base 10 to permit the skin to 'breathe' and also to permit a solvent solution to pass through the openings to dissolve the adhesive so as to facilitate removal of the support plate from the skin.

An adhesive of a medical grade is applied to the bottom surface of the support base by conventional means. This may be sprayed on or applied by use of a double sided adhesive.

A flexible membrane 28 is provided which covers the opening 35 of the hollow tubular member 12 so that any transducer in the opening is maintained away from physical contact with the patient.

It has been found that during labor, body perspiration can cause the adhesive contact with the skin to be loosened. To prevent the perspiration from loosening the adhesive, a highly absorbent material 17 is applied to the bottom surface 16 of the support base surrounding the opening in the support base. The highly absorbent material can be any number of well-known absorbent materials, including paper, such as used in breast shields, disposable diapers and sanitary napkins, sponges, and fabrics, such as cotton.

The highly absorbent material serves to restrict perspiration from coming into contact with the adhesive in the vicinity of the perimeter of the support base, reducing the likelihood that the support base will accidentally lift from the patient. The absorbent material also assists in permitting the evaporation of the perspiration through the openings 26 in the support base.

An adhesive layer 30 is attached to the bottom surface 16 of the support base which in turn is covered by a removable paper backing sheet 32.

The support base can be made by conventional molding techniques. In one instance, two different materials are deposited in the mold, one for the first inner portion and one for the second outer portion and the support base is made in one molding operation. It is also possible to make the support base in two steps, first making the first inner portion and the second outer portion and then combining them together by various conventional means, including molding, adhesive or welding.

In operation, the skin of the patient is cleansed with alcohol and then swabbed with a quick drying solution (e.g., collodion) to provide a uniform base for the adhesive as well as a readily dissolvable layer which permits easy removal of the sensor support base at the termination of the procedure.

Once the patient is prepared, the paper backing is removed from the support base and the support base is then attached to the abdomen of the patient. The support base is maintained in contact with the patient until it is desired to remove it. This is accomplished by applying a solvent, such as alcohol, through the openings 26 to the area. This can be done by spray or cloth. It has been found to be particularly advantageous to apply the solution around the periphery of the support base while gently lifting the flexible second outer portion 20 of the support base.

It has been found that on a limited number of occasions the patient has been so heavy that the standard sensor base attachment requires that additional support be provided to the base. In such cases ancillary adhesive tape 40 and 42 can be applied across the upper surface of the support base, as in FIG. 4, or across projections 50 and 52 extending from the top of the tubular member 12, as shown in Figure 5.

Figure 4:
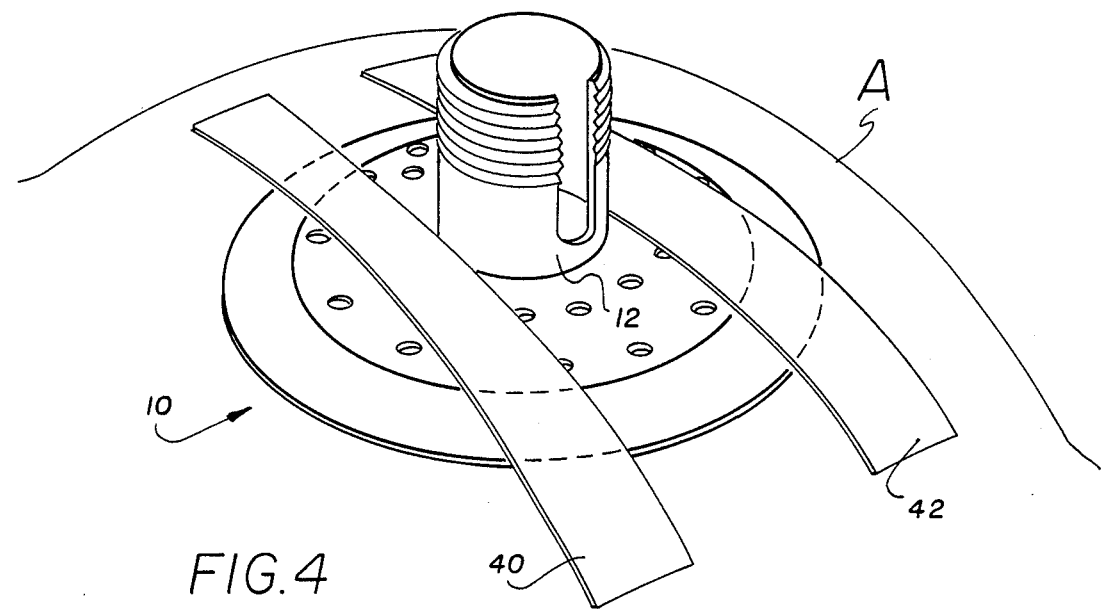
FIG. 4 is a top perspective view of an ancillary adhesive support means used with the present invention.
Figure 5:
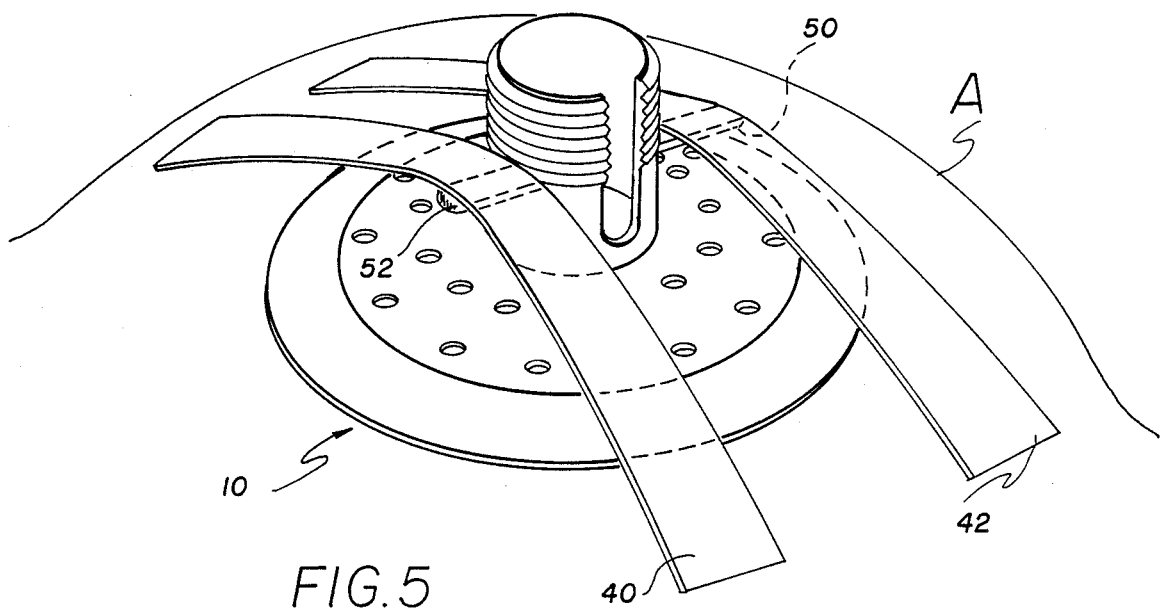
FIG. 5 is a top perspective view of an alternate embodiment of the invention with ancillary adhesive support means used with the present invention.

Referring to FIGS. 4 and 5 the ancillary adhesive means is shown maintaining the support base in place on the abdomen 100 of the patient. It is preferred, however, that the adhesive still be applied to the lower surface of the support base, with the tape being applied as secondary reinforcement. The reinforcement tape holds the skin of the patient in tension. Provided that the secondary tapes are sufficiently strong to prevent the lateral or vertical movement of the support base, the secondary tapes may be used without the double-sided adhesive on the bottom surface of the support base.

Referring to FIGS. 6 and 7, an alternative preferred embodiment is shown for assuring that the support base can be used with patients that are particularly heavy or where the ratio of the size of the patient to the size of the fetus is relatively large.

The support base 46 has on the upper surface 48, proximate the perimeter of the outer flexible portion 20, a series of equidistant loops or hooks 50, which may be formed integrally with the outer portion 20 of the support plate 46. While in the preferred embodiment of the invention there are four such loops 50, more or less than four may be employed. Also, while such loops 50 ma be formed integrally with the top surface of the support base 46, they may be separate elements that are molded or glued to the surface.

Equidistant and in alignment with the loops 50 are a series of openings 52 in a collar 54 surrounding the bottom of the hollow tubular member 12. The openings 52 have their axis in alignment parallel to the axis of the hollow tubular member 12.

A second series of upper openings 60 are formed in the hollow tubular member 12, equidistant from one another and in alignment with the loops 50. The second series of upper openings 60 are located higher on the hollow tubular member 12 than the first series of openings 52.

A third series of top openings 64 are formed in the cap 66, equidistant from one another and in alignment with the loops 50. The openings in the cap 66 are aligned when the cap is placed in the proper position.

A rigid support strut 68, is pivotally connected at one end by engaging means 70, and has at its other end a U-shaped hook 72, for fitting in and engaging the openings 52, 60 and 64. The support strut 68 is substantially rectangular in shape and of a length slightly shorter than the distance from the loop 50 to the exterior of the hollow tubular member.

In FIGS. 6 and 7 a support strut member 68 is shown having the U-shaped end 72 fitting within the different openings. The support strut 68 is substantially inflexible, being made of metal or plastic, so that when it is fitted within the openings in the hollow tubular member 12 the periphery of the support base in the vicinity of the loop 50 is substantially fixed in relationship to the hollow tubular member 12.

The operation of the device is as follows: It has been found that the adhesive on the soft flexible outer portion is maintained relatively fixed to the patient, and rarely dislodged during the labor process, notwithstanding external factors such as perspiration or the downward pressure applied on the abdomen 100 by the transducer 80. Thus, when the transducer 80 and the cap 66 are installed in the hollow tubular member, the adhesive around the periphery of the support base does not give way.

In most patients, the advancing of the pressure bearing rod 82 results in the transducer being pressed against the abdomen sufficiently so as to obtain reliable measurements of the contractions. However, on some occasions, the transducer cannot be pressed down far enough into the abdomen by advancement of the pressure bearing rod 82, to penetrate the layers of tissue separating the activity of the uterus from the transducer. In applicant's prior application it had been proposed that the hollow tubular member extend below the bottom surface 16 of the support plate 10 so that it would press down into the abdomen of a heavy patient. However, such a configuration turned out to be extremely uncomfortable, particularly if the support plate was going to be left on the patient for an extended period of time or in patients that had no need for such pressing. Accordingly it was desired to obtain a support base which could be used on either heavy or thin patients and left on the patient for a long period of time without discomfort while at the same time obtaining reliable data.

Having a relatively flexible outer ring in relationship to the relatively rigid inner ring of the support base permits the relatively rigid inner portion to be depressed, in relationship to the outer flexible portion, into the abdomen of the patient. Referring to FIGS. 7, it may be seen that once the central portion of the support plate is pushed into the abdomen of the patient, it is maintained in that depressed position relative the outer portion by means of fixing the U-shaped ends 72 of the support struts 68 in the openings 52, 60 and 64 in the hollow tubular member 12 and the cap 66. Once the support struts 68 are fixed in place, in effect the starting point of the transducer is lower in relationship to the surface of the abdomen 100 than it otherwise would have been.

Figure 7A:
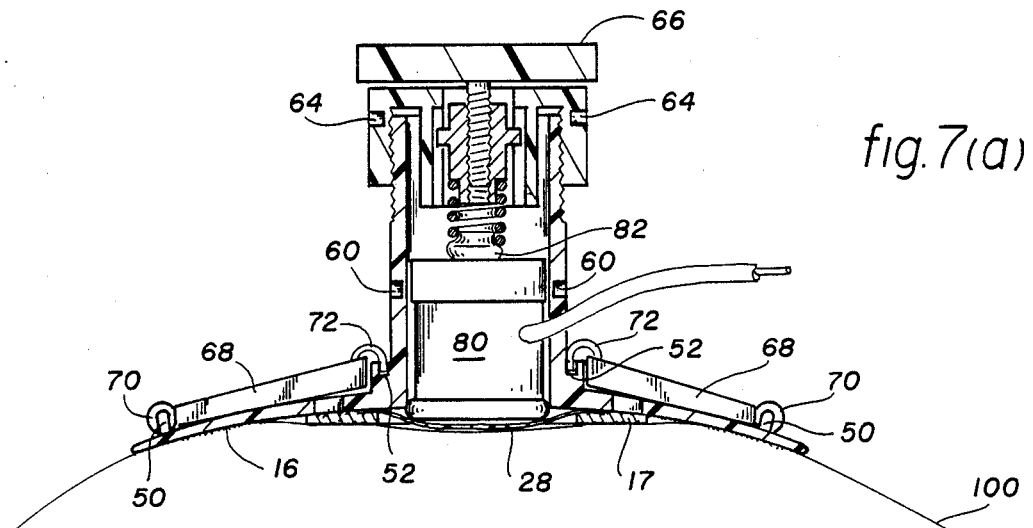
FIGS. 7(a)–(c) are side sectional views of another alternative embodiment of the present invention showing the support base in three different deformed configurations.
Figure 7B:
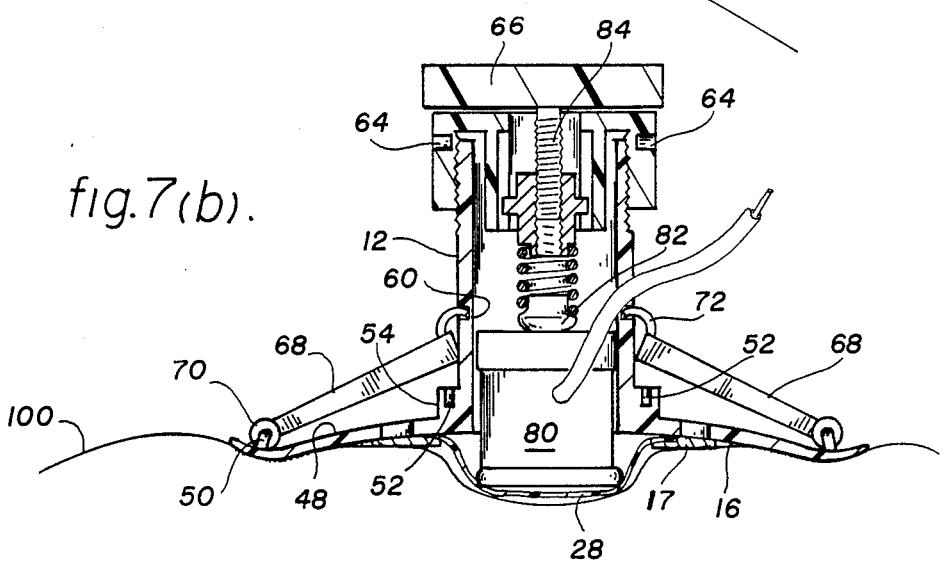
Figure 7C:
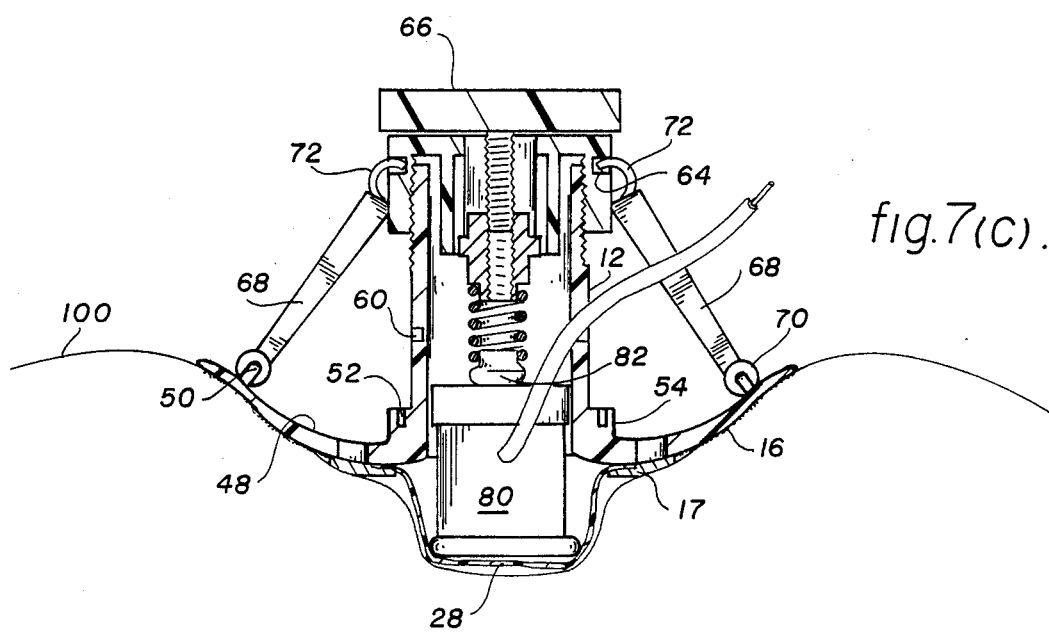

Referring to FIG. 7(a), the configuration of the support base is shown with the struts in place in openings 52. In this configuration, the inner portion is prevented from being pressed up by the abdomen. In FIG. 7(b) the support base is shown with the support struts 68 fitted within the upper openings 60 substantially deforming the support base so that the rigid inner portion is depressed in relationship to the outer portion. In FIG. 7(c) the support struts 68 are attached to the top openings 64 located in the cap 66, further deforming the shape of the support base 46 and further depressing the rigid inner portion 18.

In use, the support base 46 is attached as normal. However, if it is found that the transducer 80 that the transducer cannot be advanced far enough by advancement of pressure bearing rod 82 to provide an adequate base line from the transducer because the patient is too heavy, then the cap is loosened and then the hollow tubular member is pushed down, deforming the shape of the support base, and depressing the rigid inner portion 18 into the abdomen of the patient. The total available depression can be as much as two inches or more. The support struts 68 are inserted into the desired openings so as to maintain the support base in the deformed, depressed shape. The cap is then tightened again and the base line of the transducer then established. If the selected openings chosen were still not sufficient to provide an adequate, then the next higher series of openings are used. Experience will teach the user the desired deformation required.

The amount of deformation of the support base 46 obtainable is a function of the diameter of the support base, the length of the support strut 68, the position where the strut is attached on the surface of the support base 68 and the height of the hollow tubular member 12 and cap 66.

While the preferred embodiment discloses individual strut members 68 connected from the support base to the hollow tubular member 12 and cap 66, it is possible to use other means of maintaining the fixed relationship between the periphery of the support base and the tubular member, such as by having a flexible strut, such as a wire, pinned on one side of the support base 46 and passing over a projection or loops extending from the hollow tubular member 12, or cap 66, and then being pinned to the other side of the support base.

It is recognized that such apparatus may be employed on all contraction support plates, but it may be desirable, due to cost of manufacture, to employ such configuration only for those patients where it is believed that it will be necessary. It has been found that most patients do not require this added feature.

Also, while the apparatus has been described in association with use on the abdomen of a patient for recording contractions, the claimed invention may be readily adapted for use in the recording of other data, used at other locations of the patient, such as respiration.

While the preferred embodiment has been described, it is recognized that other variation of the present invention can be made without departing from the teachings described herein.

What is claimed is:

1. A sensor support adapted to be adhesively attached to a patient comprising a support base, said support base having an upper surface and a lower surface and having an opening therein to receive a removable pressure transducer sensor, and said support base having a first relatively rigid inner portion surrounding the opening and a distinct second relatively flexible outer portion attached to at least a portion of the periphery of said relatively rigid portion being substantially more flexible than the inner portion.

2. The sensor support of claim 1 in which the material of said second outer portion is a different type material from the material of said first inner portion.

3. The sensor support of claim 2 in which said second outer portion is made of a flexible material, selected from soft flexible plastic and soft flexible rubber.

4. The sensor support of claim 1 in which said first inner portion is made of a relatively rigid plastic.

5. The sensor support of claim 1 in which said first inner portion and said second outer portion are integral.

6. The sensor support of claim 1 in which said support base is substantially concave.

7. The sensor support of claim 6 in which said support base has an outer diameter of approximately 3 to 5 inches.

8. The sensor support of claim 6 in which said support base has an outer diameter of approximately 5 inches.

9. The sensor support of claim 6 in which said second outer portion extends substantially around the entire periphery of said first inner portion.

10. The sensor support of claim 1 in which said support base has adhesive attached to the lower surface of said support base.

11. The sensor support of claim 1 in which a flexible membrane covers said opening in said support base.

12. A sensor support comprising a support base, including means for supporting a transducer sensor, said support base having an upper and a lower surface and a moisture absorbent material on at least a portion of the lower surface of said support base which can absorb perspiration when the lower surface is applied to a patient's body.

13. The sensor support of claim 12 in which said means for supporting a transducer sensor comprises an opening and said absorbent material surrounds said opening in the support base.

14. The sensor support of claim 13 in which said absorbent material is an absorbent paper.

15. The sensor support of claim 13 in which said absorbent material is sponge.

16. The sensor support of claim 13 in which said absorbent material is fabric.

17. A sensor support adapted to be adhesively applied to the patient comprising (a) a sensor support base having an upper surface and a lower surface; (b) support means connected to said sensor support base for supporting a removable transducer sensor: said support base having a first relatively rigid inner portion surrounding said means for supporting a removable transducer and a distinct second relatively flexible outer portion surrounding said first portion, all of the material of said second outer portion being substantially more flexible than the outer periphery of said first inner portion.

18. The sensor support of claim 17 in which said second flexible portion is formed integral with said first portion.

19. The sensor support of claim 18 in which said second portion is affixed to at least a portion of the periphery of said first portion.

20. The sensor support of claim 18 in which said support base is substantially concave.

21. The sensor support of claim 20 in which said support base is substantially circular.

22. The apparatus of claim 17 in which said first portion and said second portion are normally substantially in the same first plane and one of said portions is deformable in relationship to said other portion by application of pressure, whereby one said portion may be moved out of said first plane.

23. The sensor support of claim 22 including receptacle means for affixing one end of a relatively rigid member to the upper surface of the support base and a second end of the relatively rigid member to the means for supporting said transducer sensor to maintain said first and second portions in different planes.

24. The apparatus of claim 23, in which said receptacle means comprises openings in said means for supporting said transducer sensor.

25. The apparatus of claim 23 in which the lower surface of the relatively flexible portion of the support base has an adhesive layer thereon.

26. The apparatus of claim 17 including maintaining means for maintaining said first and second portions in different planes.

27. The apparatus of claim 26 in which said maintaining means comprises at least one rigid strut member fixed at one end to said second portion and capable of attachment at another end to a second member attached to said first portion.

28. The apparatus of claim 27 in which said second member comprises means for supporting a transducer sensor.

29. The apparatus of claim 26 in which said maintaining means comprises at least one flexible strut fixed at one end to one of the portions and capable of being fixed at a second position on the support base.

30. A sensor support comprising (a) a sensor support base; (b) a means for supporting a sensor connected to said sensor support base, said means for supporting a sensor having at least one projection extending therefrom for supporting an adhesive means which can pass thereover and adhesively attach to the body of a patient to assist in holding said support base thereagainst.

31. The apparatus of claim 22 in which there are at least two projections for supporting surgical tape.

32. A sensor support comprising a relatively rigid support base connected to means for supporting a sensor, said sensor support base having an upper and a lower surface, said lower surface having an absorbent material affixed thereto which can absorb perspiration when the lower surface is applied to a patients body.

33. The apparatus of claim 32 in which said support base has a series of openings therethrough.

34. The apparatus of claim 32 in which said absorbent material is absorbent paper.

35. The apparatus of claim 32 in which said absorbent material is sponge.

36. The apparatus of claim 32 in which said absorbent material comprises a fabric.

37. The apparatus of claim 32 including adhesive means on the outer periphery of the lower surface and said absorbent material being spaced away from said adhesive means.

38. The apparatus of claim 32 in which said support base includes a relatively flexible portion around its periphery.

39. A sensor support comprising (a) a sensor support base having an upper surface and a lower surface; (b) means connected to said sensor support base for supporting a transducer sensor; said support base having a first relatively rigid inner portion and a second relatively flexible outer portion, attached to at least a portion of the periphery of said relatively rigid first inner portion, including receptacle means for affixing one end of a relatively rigid member to the upper surface of the support base and a second end of the relatively rigid member to the means for supporting said transducer sensor.

40. The apparatus of claim 39 in which said first rigid portion is movable in relationship to said second relatively flexible portion such that the rigid member when affixed by said receptacle means, can maintain said first and second portions in a fixed relationship to one another.

41. The apparatus of claim 40 in which said receptacle means comprises openings in said means for supporting said transducer means.

42. The apparatus of claim 39 in which the lower surface of the relatively flexible portion of the support base has an adhesive layer thereon.

43. A sensor support comprising (a) a sensor support base having an upper surface and a lower surface; (b) means connected to said sensor support base for supporting a transducer sensor; said support base having a first relatively rigid portion and a second relatively flexible portion; said first relatively rigid inner portion being deformable in relationship to said second relatively flexible outer portion by application of pressure, and including maintaining means for maintaining said first and second portions in different planes, said maintaining means comprising at least one rigid strut member fixed at one end to said second portion and capable of attachment at another end to a second member attached to said first portion.

44. The apparatus of claim 43 in which said second member comprises means for supporting a transducer sensor.

45. The apparatus of claim 43 in which said maintaining means comprises at least one flexible strut fixed at one end to one of the portions and capable of being fixed at a second position on the support base.

46. The apparatus of claim 43 in which said maintaining means comprises at least one rigid strut fixed at one end to one of the portions and capable of being fixed at a second position on the support base.

* * * * *